(12) United States Patent
Wang

(10) Patent No.: US 12,274,424 B2
(45) Date of Patent: Apr. 15, 2025

(54) SPECIMEN RETRIEVAL DEVICE WITHOUT INTRODUCING HANDLE FOR MINIMALLY INVASIVE SURGERY AND METHOD FOR USE THEREOF

(71) Applicant: VHMED (Nantong) Co. Ltd., Nantong (CN)

(72) Inventor: Haiying Wang, Nantong (CN)

(73) Assignee: VHMED (Nantong) Co. Ltd., Nantong (CN)

(*) Notice: Subject to any disclaimer, the term of this patent is extended or adjusted under 35 U.S.C. 154(b) by 820 days.

(21) Appl. No.: 17/376,358

(22) Filed: Jul. 15, 2021

(65) Prior Publication Data

US 2021/0401419 A1 Dec. 30, 2021

Related U.S. Application Data

(63) Continuation of application No. PCT/CN2020/111109, filed on Aug. 25, 2020.

(30) Foreign Application Priority Data

Jun. 28, 2020 (CN) .......................... 202010596955.3

(51) Int. Cl.
*A61B 17/00* (2006.01)

(52) U.S. Cl.
CPC ................ *A61B 17/00234* (2013.01); *A61B 2017/00287* (2013.01)

(58) Field of Classification Search
CPC .... A61B 17/00234; A61B 2017/00287; A61B 2017/0053; A61B 2017/00862
See application file for complete search history.

(56) References Cited

U.S. PATENT DOCUMENTS 5,037,379 A * 8/1991 Clayman .......... A61B 17/00234
128/850
5,074,867 A * 12/1991 Wilk ................ A61B 17/00234
604/93.01

(Continued)

FOREIGN PATENT DOCUMENTS

CN 1608593 A 4/2005
CN 203898360 U 10/2014

(Continued)

OTHER PUBLICATIONS

First Office Action issued in counterpart Chinese Patent Application No. 202010596955.3, dated Aug. 24, 2022.

(Continued)

*Primary Examiner* — Mohamed G Gabr
(74) *Attorney, Agent, or Firm* — Westbridge IP LLC

(57) ABSTRACT

Disclosed is a specimen retrieval device without introducing handle for minimally invasive surgery, which includes an endobag, a variable-diameter assembly for endobag collection and release, an elastic opening expansion mechanism and an opening closure assembly. The variable-diameter assembly for endobag collection and release is a cylindrical structure formed by curling an elastic sheet-shaped object, and in a natural state, two ends of the elastic sheet-shaped object are partially overlapped and separated from each other. The elastic opening expansion mechanism and the opening closure assembly are disposed in an opening of the endobag. The endobag is placed in the variable-diameter assembly for endobag collection and release; and the variable-diameter assembly for endobag collection and release is placed in a trocar cannula.

13 Claims, 3 Drawing Sheets

(56) References Cited

U.S. PATENT DOCUMENTS

| | | | |
|---|---|---|---|
| 5,341,815 A * | 8/1994 | Cofone | A61B 17/00234 600/562 |
| 7,837,612 B2 | 11/2010 | Gill et al. | |
| 8,075,567 B2 | 12/2011 | Taylor et al. | |
| 8,870,894 B2 | 10/2014 | Taylor et al. | |
| 9,414,817 B2 | 8/2016 | Taylor et al. | |
| 2010/0152609 A1 | 6/2010 | Zwolinski et al. | |
| 2011/0190780 A1* | 8/2011 | O'Prey | A61B 17/221 606/114 |
| 2012/0083877 A1* | 4/2012 | Nguyen | A61F 2/2436 623/2.11 |
| 2016/0262739 A1 | 9/2016 | O'Prey et al. | |
| 2016/0324515 A1 | 11/2016 | Ravikumar et al. | |

FOREIGN PATENT DOCUMENTS

| | | |
|---|---|---|
| CN | 104368080 A | 2/2015 |
| CN | 104771222 A | 7/2015 |
| CN | 106618747 A | 5/2017 |
| CN | 108992147 A | 12/2018 |
| CN | 210228209 U | 4/2020 |
| EP | 2668907 A2 | 12/2013 |
| JP | H07328013 A | 12/1995 |
| JP | H08103501 A | 4/1996 |
| KR | 101739225 B1 | 5/2017 |
| WO | 2005025427 A1 | 3/2005 |

OTHER PUBLICATIONS

Supplementary European Search Report issued in counterpart Europe Patent Application No. 20914761.0, dated Jan. 30, 2024.

* cited by examiner

SPECIMEN RETRIEVAL DEVICE WITHOUT INTRODUCING HANDLE FOR MINIMALLY INVASIVE SURGERY AND METHOD FOR USE THEREOF

CROSS-REFERENCE TO RELATED APPLICATIONS

The application is a continuation of International Application No. PCT/CN2020/111109, filed on Aug. 25, 2020, which claims priority to Chinese Patent Application No. 202010596955.3, filed on Jun. 28, 2020. The disclosures of the aforementioned applications are hereby incorporated by reference in their entireties.

TECHNICAL FIELD

The disclosure relates to the technology field of medical apparatus, in particular to a specimen retrieval device without introducing handle for minimally invasive surgery and a method for use thereof.

BACKGROUND

With the development of endoscope techniques and the continuous launch of advanced minimally invasive surgical instruments, minimally invasive surgery has been widely popularized. There are certain space limitations in surgical operations under an endoscope, so that a specially designed surgical specimen retrieval device, used for a tissue specimen and surgical resection in a minimally invasive surgery scene, is widely used in various minimally invasive surgeries.

There are usually two designs for the surgical specimen retrieval device used for retrieving a tissue specimen and surgical resection: one is with an introducing rod, while the other is not. An endobag is usually made of a long tapered water-proof fiber or polymer material; and the introducing rod is usually made of an introducing handle combined with a metal or plastic pipe. During minimally invasive surgery, the endobag is delivered into a patient cavity through an instrument channel by the operation of the introducing handle. Then the tissue specimen or surgical resection is put inside the endobag, and the endobag is securely closed by an operation of pulling a drawstring at the introducing handle and is retrieved through the instrument channel.

The specimen retrieval device with introducing rod has the characteristics of convenient operation and safe use and so on. It is, however, complex to manufacture and high in cost, and its working diameter is restricted by the designed outer diameter of its introducing rod, so it has a higher requirement for a trocar used with it that the inner diameter of the trocar must be larger than the outer diameter of the introducing rod of the specimen retrieval device.

The specimen retrieval device without introducing rod is simply designed and structured, but it is less convenient to use and cannot be opened easily after entering the body cavity. An atraumatic instrument is required to bring the endobag into a patient cavity through a trocar cannula, to avoid damage to the endobag by the instrument during a surgical process, which can cause a failure of specimen retrieval. Taking the convenience of operation into account, some specimen retrieval devices without introducing handle on the market are designed with an insertion tube. The endobag is rolled into the insertion tube and is inserted into a trocar cannula during the operation, to facilitate the endobag to enter the patient's body cavity, but this is also restricted by the diameters of the cannula and trocar.

SUMMARY

The technical problem to be solved by the disclosure is to provide a specimen retrieval device without introducing handle for minimally invasive surgery, so that it solves the shortcomings of the traditional specimen retrieval device with introducing handle, which is complicated in design and restricted by the working outer diameter.

In order to solve the above technical problem, the disclosure adopts the following technical solutions, a specimen retrieval device without introducing handle for minimally invasive surgery, including: an endobag, a variable-diameter assembly for endobag collection and release, an elastic opening expansion mechanism, and an opening closure assembly;

wherein the variable-diameter assembly for endobag collection and release is a cylindrical structure formed by curling an elastic sheet-shaped object, and in a natural state, two ends of the elastic sheet-shaped object are partially overlapped and separated from each other;

when an outer wall of the cylindrical structure is squeezed by an external force, an area of an overlapped part of the two ends of the elastic sheet-shaped object gradually increases, and a diameter of the cylindrical structure gradually decreases;

when an inner wall of the cylindrical structure is expanded by the external force, the area of the overlapped part of the two ends of the elastic sheet-shaped object gradually decreases, and the diameter of the cylindrical structure gradually increases;

the elastic opening expansion mechanism and the opening closure assembly are disposed in an opening of the endobag;

the elastic opening expansion mechanism automatically expands the opening of the endobag when the external force is not applied; and the opening closure assembly closes the opening of the endobag by overcoming an expansion effect of the elastic opening expansion mechanism on the opening;

the endobag is placed in the variable-diameter assembly for endobag collection and release; and the variable-diameter assembly for endobag collection and release is placed in a trocar cannula.

Advantageously, a hollow annular edge is disposed on the opening of the endobag; and the annular edge is sleeved on the elastic opening expansion mechanism and the opening closure assembly.

Advantageously, the elastic opening expansion mechanism is an annular elastic wire; a first perforation is disposed on one end of the annular elastic wire, and another end passes through the first perforation and is fixedly connected with the opening closure assembly.

Advantageously, the annular elastic wire is made of a medical grade elastic material.

Advantageously, the opening closure assembly has a drawstring; a second perforation is disposed on one end of the drawstring, and another end passes through the second perforation for a hand grasp operation.

Advantageously, the drawstring is made of a rough medical grade synthetic fiber.

Advantageously, an upper side wing is disposed on the variable-diameter assembly for endobag collection and release.

Advantageously, a bag portion of the endobag is made of a textile or polymer material.

A method for using the specimen retrieval device without introducing handle for minimally invasive surgery in this disclosure, including the following steps:

(1) folding an endobag from bottom to top into a shape to facilitate entering a variable-diameter assembly for endobag collection and release, and applying an external force to an elastic opening expansion mechanism to close an opening of the endobag;
(2) putting the folded endobag into the variable-diameter assembly for endobag collection and release;
(3) putting the variable-diameter assembly for endobag collection and release into a trocar cannula, wherein an end of a drawstring is located outside the trocar cannula;
(4) pushing the variable-diameter assembly for endobag collection and release out of the trocar cannula with a help of an instrument.

Advantageously, a folding manner of the endobag in step (1) is folding the endobag into a wave shape.

The benefits of the present disclosure include manufacturability, production cost, environmental friendly, ease of use, and ergonomics, and solving the problem of complicated design and restricted by the working outer diameters of traditional specimen retrieval devices with introducing handle. At the same time, it solves the weak point that the specimen retrieval device without introducing handle, which is inconvenient to enter and exit the patient cavity through a series of unique designs.

BRIEF DESCRIPTION OF DRAWINGS

In order to explain the technical solutions in the embodiments of the present disclosure more clearly, the following will briefly introduce the drawings needed in the embodiments. Obviously, the drawings in the following description are only some of the embodiments recorded in the present disclosure. For those of ordinary skill in the art, other drawings can be obtained based on these drawings without creative work.

DETAILED DESCRIPTION OF THE EMBODIMENTS

Figure 1:
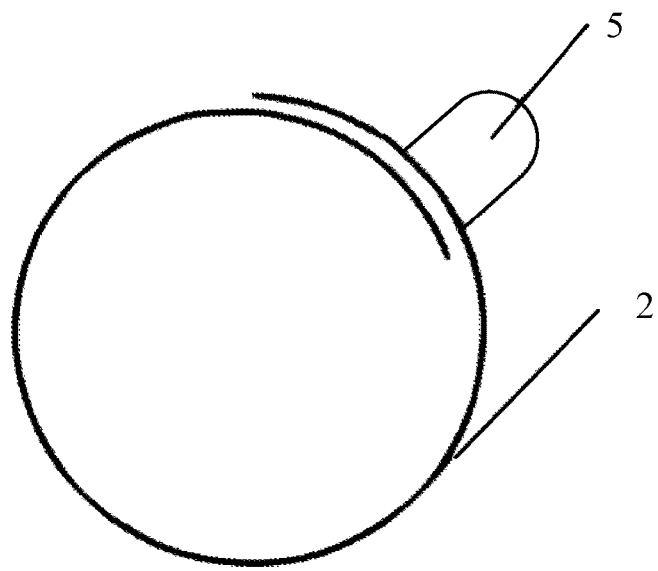
FIG. 1 is a side view of a variable-diameter assembly for endobag collection and release of this disclosure.

The technical solution of the present disclosure will be clearly and completely described below through specific implementations.

In the description of the present disclosure, it should be understood that the orientation or positional relationship indicated by the terms "middle", "top", "bottom", "inner", "outer" and so on are based on the orientation or positional relationship shown in the drawings. And this is for the convenience of describing the present disclosure and simplifying the description, rather than indicating or implying that the device or element referred to must have a specific orientation, or be constructed and operated in a specific orientation, and therefore cannot be understood as a limitation of the present disclosure. The terms "first" and "second" are only used for descriptive purposes, and cannot be understood as indicating or implying relative importance or implicitly indicating the number of technical features indicated. Thus, the features defined with "first" and "second" may explicitly or implicitly include one or more of these features. In the description of the present disclosure, "plurality" means two or more, unless otherwise specifically defined.

In addition, unless otherwise clearly specified and limited, the terms "install", "connection", "connected", "fix" and other terms should be understood in a broad sense, for example, may be a fixed connection, detachable connection, or integral ground connection; may be a mechanical connection or an electrical connection; may be directly connected, indirectly connected through an intermediate medium, or internal communication between two components. For those of ordinary skill in the art, the specific meaning of the above-mentioned terms in the present disclosure can be understood according to the specific situation.

In the present disclosure, unless otherwise clearly defined and restricted, the first feature being "above" or "below" the second feature may include direct contact between the first and second features, or the first and second features not in direct contact but through other features between them. Moreover, the first feature being "above", "on", and "over" the second feature may include the first feature being directly above and obliquely above the second feature, or simply means that the first feature has a higher horizontal height than the second feature. The first feature being "beneath", "below", "under" the second feature includes the first feature being directly below and obliquely below the second feature, or simply means that the horizontal height of the first feature is less than that of the second feature.

Figure 2:
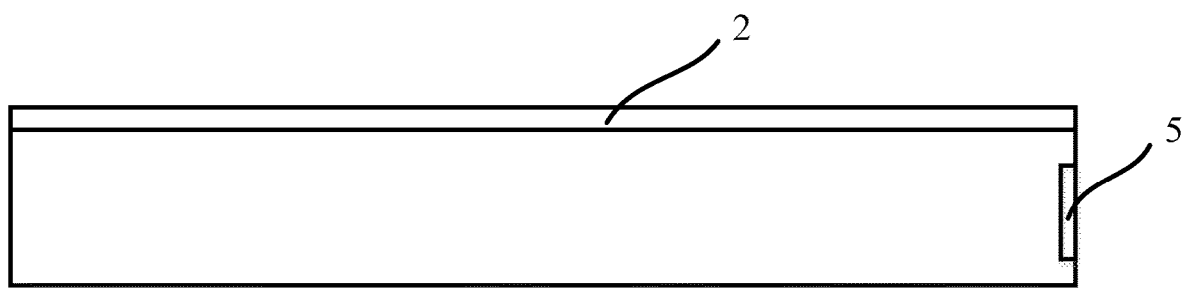
FIG. 2 is a front view of a variable-diameter assembly for endobag collection and release of this disclosure.
Figure 3:
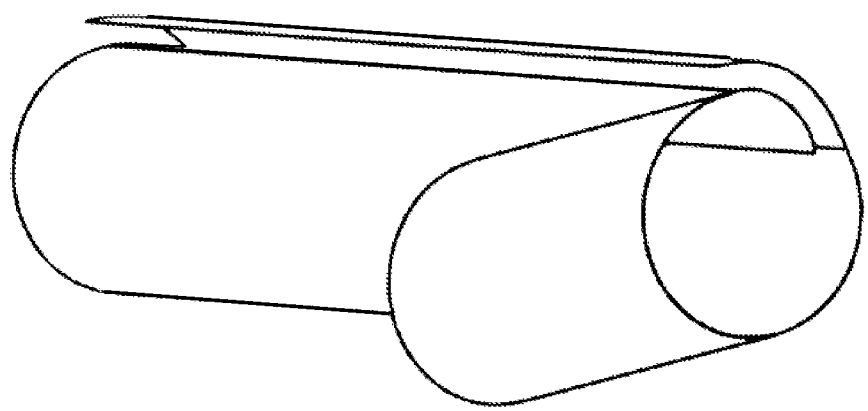
FIG. 3 is a stereogram of a variable-diameter assembly for endobag collection and release of this disclosure.
Figure 4:
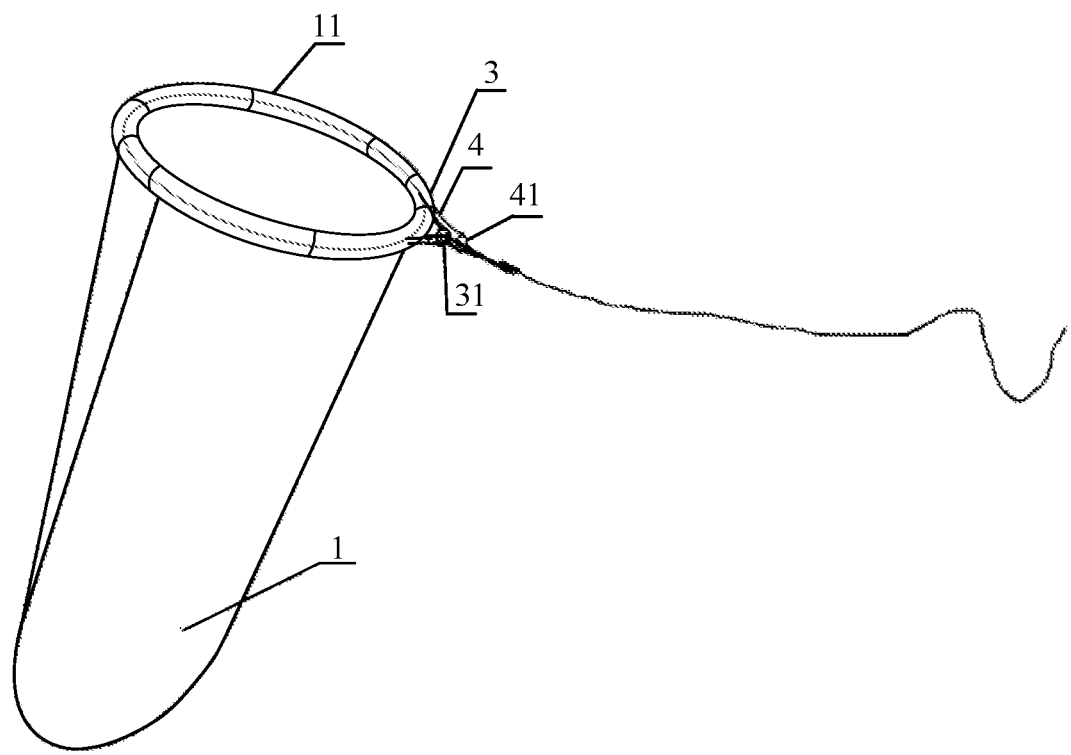
FIG. 4 is a structure schematic diagram of an endobag of this disclosure.
Figure 5:
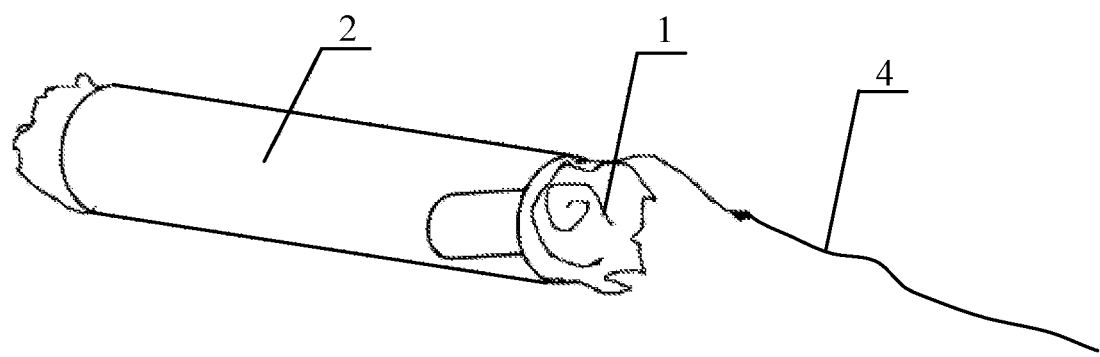
FIG. 5 is a state diagram illustrating an endobag put into a variable-diameter assembly for endobag collection and release of the present disclosure.

Referring to FIG. 1 to FIG. 5, a specimen retrieval device without introducing handle for minimally invasive surgery of this disclosure includes: an endobag 1, a variable-diameter assembly for endobag collection and release 2, an elastic opening expansion mechanism 3 and an opening closure assembly 4.

The variable-diameter assembly for endobag collection and release 2 is a cylindrical structure formed by curling an elastic sheet-shaped object, and in a natural state, two ends of the elastic sheet-shaped object are partially overlapped and separated from each other. Preferably, an upper side wing 5 is disposed on the variable-diameter assembly for endobag collection and release in this disclosure. When the variable-diameter assembly for endobag collection and release 2 is put inside a trocar cannula, the upper side wing is left outside of the trocar cannula, which will restrict the position of the variable-diameter assembly for endobag collection and release, and prevent the variable-diameter assembly for endobag collection and release 2 from completely falling into the trocar cannula and entering the patient cavity through the trocar cannula. The upper side wing 5 is provided with features of convenient operation and prevention of misoperation. Preferably, the upper side wing 5 is arranged at an end of the cylindrical structure.

When an outer wall of the cylindrical structure is squeezed by an external force, an area of the overlapped part of the two ends of the elastic sheet-shaped object gradually increases, and a diameter of the cylindrical structure gradually decreases.

When an inner wall of the cylindrical structure is expanded by an external force, the area of the overlapped part of the two ends of the elastic sheet-shaped object gradually decreases, and the diameter of the cylindrical structure gradually increases.

The variable-diameter assembly for endobag collection and release 2 is placed in the trocar cannula.

The configuration of the cylindrical structure of the variable-diameter assembly for endobag collection and release can be adapted to different specifications and sizes of endobags and trocar cannulas. When there is a large endobag placed into the variable-diameter assembly for endobag collection and release, the inner wall of the cylindrical structure is stressed by the internal endobag, so that the cylindrical structure is gradually expanded and the diameter is increased to accommodate the endobag. When the cylindrical structure is to enter a relatively small inner diameter of the trocar cannula, the outer wall of the cylindrical structure is squeezed by hand to reduce the diameter of the cylindrical structure, thus entering the trocar cannula smoothly.

The elastic opening expansion mechanism 3 and the opening closure assembly 4 are disposed in an opening of the endobag 1 in this disclosure.

The elastic opening expansion mechanism 3 automatically expands the opening of the endobag when no external force is applied; and the opening closure assembly 4 closes the opening of the endobag by overcoming an expansion effect of the elastic opening expansion mechanism.

A hollow annular edge 11 is disposed on the opening of the endobag 1; and the annular edge 11 is sleeved on the elastic opening expansion mechanism 3 and the opening closure assembly 4.

The elastic opening expansion mechanism 3 is an annular elastic wire; a first perforation 31 is disposed on one end of the annular elastic wire, and the other end passes through the first perforation 31 and is fixedly connected with the opening closure assembly 4. The annular elastic wire is a medical grade elastic material, which has the characteristics of good opening performance and easy to be placed.

The annular elastic wire of the present disclosure can easily deform when a very small external force is applied to the annular elastic wire, and it will immediately return to its original shape when the external force is removed. The annular elastic wire is made of a medical grade elastic material, so that it is easy to squeeze and place the elastic opening expansion mechanism inside the variable-diameter assembly for endobag collection and release. When the annular elastic wire is placed inside the cylindrical structure, the stress to the inner wall of the cylindrical structure by the annular elastic wire is not sufficient to deform the cylindrical structure. The elastic opening expansion mechanism instantly returns to its original shape after the endobag enters the body cavity to expand the opening of the endobag.

The opening closure assembly has a drawstring in this disclosure; a second perforation 41 is disposed on one end of the drawstring, and the other end passes through the second perforation 41 for hand to grasp. The drawstring is made of a rough medical grade synthetic fiber, which has the advantage of being easy to pull and not cutting hands.

The bag portion of the endobag of the present disclosure is synthesized by a textile or polymer material, and has the characteristics of good strength, thin thickness, leakage prevention and the like combined with sewing, heat sealing and other processes.

When retrieving surgical specimens of the present disclosure, one end of the drawstring remaining outside of the trocar cannula is pulled, one end of the annular elastic wire is driven to close by the drawstring, and the drawstring is pulled continuously to pull the endobag into the trocar cannula for retrieving.

The present disclosure provides a method for using the specimen retrieval device without introducing handle for minimally invasive surgery, including the following steps:
(1) folding an endobag from bottom to top into a shape that can enter the variable-diameter assembly for endobag collection and release, and applying an external force to the elastic opening expansion mechanism to close the opening of the endobag;
(2) putting the folded endobag into the variable-diameter assembly for endobag collection and release;
(3) putting the variable-diameter assembly for endobag collection and release into a trocar cannula, wherein an end of the drawstring is located outside the trocar cannula;
(4) pushing the variable-diameter assembly for endobag collection and release out of the trocar cannula by means of an instrument;
(5) pulling the drawstring to tighten the opening of the endobag after the surgical specimen is placed inside the endobag;
(6) pulling the drawstring continuously to remove the endobag out of the patient cavity from the trocar cannula.

A manner of folding the endobag in step (1) includes folding the endobag into a wave shape. The endobag folded into a wave shape can be quickly opened without the help of an external instrument when it enters the patient body.

The above-mentioned embodiments are only descriptions of preferred embodiments of the present disclosure, and are not intended to limit the concept and scope of the present disclosure. Without departing from the design concept of the present disclosure, the various modifications and improvements made by those of ordinary skill in the art should fall within the protection scope of the present disclosure, and the technical content claimed in the present disclosure has all been recorded in the claims.

What is claimed is:
1. A specimen retrieval device without an introducing handle for minimally invasive surgery, comprising an endobag, a variable-diameter assembly for endobag collection and release, an elastic opening expansion component, and an opening closure component,
wherein the variable-diameter assembly for endobag collection and release is a cylindrical structure formed by curling an elastic sheet-shaped object, and in a natural state, two ends of the elastic sheet-shaped object are partially overlapped and separated from each other;
when an outer wall of the cylindrical structure is squeezed by an external force, an area of an overlapped part of the two ends of the elastic sheet-shaped object gradually increases, and a diameter of the cylindrical structure gradually decreases;
when an inner wall of the cylindrical structure is expanded by the external force, the area of the overlapped part of the two ends of the elastic sheet-shaped object gradually decreases, and the diameter of the cylindrical structure gradually increases; and
the elastic opening expansion component and the opening closure component are disposed in an opening of the endobag,
wherein the elastic opening expansion component is an annular elastic wire; a first perforation is disposed on one end of the annular elastic wire, and another end passes through the first perforation and is fixedly connected with the opening closure component;

wherein when the annular elastic wire is placed in the cylindrical structure, stress to the inner wall of the cylindrical structure by the annular elastic wire is not sufficient to deform the cylindrical structure.

2. The specimen retrieval device of claim 1, wherein the elastic opening expansion component automatically expands the opening of the endobag when the external force is not applied; and the opening closure component closes the opening of the endobag by overcoming an expansion effect of the elastic opening expansion component on the opening.

3. The specimen retrieval device of claim 1, wherein the endobag is placed in the variable-diameter assembly for endobag collection and release.

4. The specimen retrieval device of claim 1, wherein the variable-diameter assembly for endobag collection and release is placed in a trocar cannula.

5. The specimen retrieval device of claim 1, wherein a hollow annular edge is disposed on the opening of the endobag; and the annular edge is sleeved on the elastic opening expansion component and the opening closure component.

6. The specimen retrieval device of claim 1, wherein the annular elastic wire is a medical grade elastic material.

7. The specimen retrieval device of claim 1, wherein the opening closure component has a drawstring; a second perforation is disposed on one end of the drawstring, and another end passes through the second perforation for a hand grasp operation.

8. The specimen retrieval device of claim 7, wherein the drawstring is made of a rough medical grade synthetic fiber.

9. The specimen retrieval device of claim 1, wherein an upper side wing is disposed on the variable-diameter assembly for endobag collection and release.

10. The specimen retrieval device of claim 9, wherein the upper side wing is disposed at an end of the cylindrical structure.

11. The specimen retrieval device of claim 1, wherein a bag portion of the endobag is made of a textile material or a polymer material.

12. A method for using a specimen retrieval device without an introducing handle for minimally invasive surgery, wherein the specimen retrieval device comprises an endobag, a variable-diameter assembly for endobag collection and release, an elastic opening expansion component, and an opening closure component;

the variable-diameter assembly for endobag collection and release is a cylindrical structure formed by curling an elastic sheet-shaped object, and in a natural state, two ends of the elastic sheet-shaped object are partially overlapped and separated from each other;

when an outer wall of the cylindrical structure is squeezed by an external force, an area of an overlapped part of the two ends of the elastic sheet-shaped object gradually increases, and a diameter of the cylindrical structure gradually decreases;

when an inner wall of the cylindrical structure is expanded by the external force, the area of the overlapped part of the two ends of the elastic sheet-shaped object gradually decreases, and the diameter of the cylindrical structure gradually increases;

the elastic opening expansion component and the opening closure component are disposed in an opening of the endobag;

wherein the method comprising the following steps:

folding the endobag from bottom to top into a shape to facilitate entering the variable-diameter assembly for endobag collection and release, and applying an external force to the elastic opening expansion component to close the opening of the endobag;

putting the folded endobag into the variable-diameter assembly for endobag collection and release;

putting the variable-diameter assembly for endobag collection and release into a trocar cannula, wherein an end of a drawstring is located outside the trocar cannula; and pushing the variable-diameter assembly for endobag collection and release out of the trocar cannula with a help of an instrument, wherein the elastic opening expansion component is an annular elastic wire; a first perforation is disposed on one end of the annular elastic wire, and another end passes through the first perforation and is fixedly connected with the opening closure component;

wherein when the annular elastic wire is placed in the cylindrical structure, stress to the inner wall of the cylindrical structure by the annular elastic wire is not sufficient to deform the cylindrical structure.

13. The method of claim 12, wherein folding the endobag from bottom to top into a shape includes folding the endobag into a wave shape.

* * * * *